United States Patent [19]

Sarazin

[11] Patent Number: 5,326,351
[45] Date of Patent: Jul. 5, 1994

[54] PROSTHESIS FITTING DEVICE

[76] Inventor: Maurice Sarazin, 123 Rue des Colverts, 34400 Lunel, France

[21] Appl. No.: 946,419

[22] PCT Filed: Jun. 7, 1991

[86] PCT No.: PCT/FR91/00453
§ 371 Date: Nov. 6, 1992
§ 102(e) Date: Nov. 6, 1992

[87] PCT Pub. No.: WO91/18564
PCT Pub. Date: Dec. 12, 1991

[30] Foreign Application Priority Data

Jun. 7, 1990 [FR] France .................. 90 07452

[51] Int. Cl.⁵ ............................ A61F 2/80; A61F 2/60
[52] U.S. Cl. ........................................ 623/33; 623/34;
623/27; 223/111
[58] Field of Search ..................... 623/27, 33, 34, 38;
294/115; 223/111, 112

[56] References Cited

U.S. PATENT DOCUMENTS 3,651,958  3/1972  Evans et al. .................. 294/115 X
3,922,727 12/1975  Bianco .
4,038,701  8/1977  McFall et al. ..................... 623/34
4,892,239  1/1990  Tomasi ............................ 223/111

FOREIGN PATENT DOCUMENTS 806981   4/1951  Fed. Rep. of Germany .
8514423  7/1985  Fed. Rep. of Germany .
2506150 11/1982  France .

Primary Examiner—Randall L. Green
Assistant Examiner—D. Willse
Attorney, Agent, or Firm—Young & Thompson

[57] ABSTRACT

A jersey sheath drawing device for fitting contact prostheses, whereby an upper or lower limb amputee can easily put on his own prosthesis. The workload of hospital staff assigned to assisting amputees in specialized rehabilitation centres can also be reduced. The device comprises a bearing (10) designed to rest on the rim of the opening (2) at the end of the nest (1) of the prosthesis, a self-locking catch (12) for tightly gripping the jersey sheath (1B) across the whole or only a part of its cross-section, a pulling runner (11) sliding on a sliding frame (6) and controlling the locking catch (12). The pulling runner (11) can be moved manually by means of the handles (6A, 8) or electrically by means of an endless screw driven by a motor. The device allows both the prosthesis (1) to be guided towards the stump (1A) for fitting thereto and the sheath (1B) to be pulled tight while using only one hand, the device staying in place throughout the process. The handles (6A, 8) are ideally placed from an ergonomical point of view, both for the amputee himself and for a third party.

17 Claims, 8 Drawing Sheets

PROSTHESIS FITTING DEVICE

FIELD OF THE INVENTION

The present invention concerns a jersey sheath drawing device for fitting contact prostheses. It enables a lower or upper limb amputee to fit their prosthesis without assistance and without effort. It can also reduce the workload of hospital staff assigned to assisting amputees in specialized rehabilitation centers.

The device comprises a bearing (10) designed to rest on the rim of the opening (2) at the end of the nest (1) of the prosthesis, a self-locking catch (12) for tightly gripping the jersey sheath (1B) around the whole or only a part of its cross-section, a pulling runner (11) sliding on a sliding frame (6) and controlling the self-locking catch (12). The pulling runner (11) can be moved manually by means of handles (6A, 8) or electrically by means of an endless screw driven by a motor.

The device allows both the prosthesis (1) to be guided towards the stump (1A) to which it is to be fitted and the sheath (1B) to be pulled tight using only one hand, the device staying in place throughout the process of its own accord. The handles (6A, 8) are ideally, placed from the ergonomical point of view, either for the amputee himself or for a third party.

The present invention concerns a device enabling an upper or lower limb amputee to fit his contact prosthesis without help and without significant effort or facilitating the workload of hospital staff in specialized rehabilitation centers for amputees.

BACKGROUND OF THE INVENTION

The standard practice for fitting such prostheses requires first the fitting of a jersey sheath which is threaded over the stump like a sock. The sheath is much longer than the stump and its free end is threaded through the interior of the nest of the prosthesis and out through the air extraction valve opening at the closed end of the nest, as close as possible to the longitudinal axis of the latter. The amputee, or more usually a third person, then pulls on the free end of the jersey sheath protruding from the nest to compress the flesh of the stump and then to cause it to enter the nest and finally to extract the jersey sheath entirely from the prosthesis, by causing it to slide between the flesh of the stump and the inside wall of the nest.

The drawbacks of this fitting method are as follows:

the traction force to be exerted on the free end of the jersey sheath is far from negligible and is difficult even for a non-handicapped third person; exerting this force becomes extremely difficult or even impossible for an amputee, especially an elderly person or one fatigued by their handicap or who has difficulties in using their hands; this very high traction force requires the jersey sheath to be gripped very strongly by the hand of the person carrying out the operation, and it is often necessary to loop the material around the hand to be able to pull on it effectively; this is very tiresome, especially for rehabilitation center staff who have to repeat this operation several times daily during rehabilitation sessions; in difficult cases it is very often necessary to pull on some specific part of the circumference of the jersey sheath to cause it to slip preferentially on generatrices in contact with the softer tissues;

the direction in which the traction force must be applied is, from the ergonomical point of view, hardly compatible with human anatomy; it is easier to pull towards the body rather than away from it; for this reason there have been proposed devices with a pulley wheel and block and tackle arrangement pressed onto the floor by the sound foot of a lower limb amputee in order to reverse the direction of the force and to reduce it through the mechanical advantage of this device (see the patent FR 2.506,150, for example); systems of this kind have not been widely adopted because they apply to special cases and do not solve the problem of guiding the prosthesis during fitting.

The same applies to devices of the type including a motor resting on the floor, controlled by the amputee and having a shaft around which the jersey sheath can be wound and unwound, as described in the U.S. Pat. No. 3,922,727.

As previously mentioned, during the fitting of the prosthesis it is also necessary to hold the prosthesis and to guide it towards the stump. This is because the friction forces due to movement of the jersey sheath through the air extraction valve opening tend to draw the nest away from the stump rather than towards it.

SUMMARY OF THE INVENTION

The present invention claims to remedy the above drawbacks in that the device in accordance with the invention comprises force amplifier means enabling a very high, progressive and sensitively controllable contraction force to be applied to the jersey sheath and in that the device comprises means for holding the jersey sheath enabling it to be pulled either around its entire circumference or over part only of the latter, and in that the device comprises means for bearing engagement at the closed end of the prosthesis around the air extraction valve orifice, and in that the reaction to the traction force is exerted at this bearing point, the effect of which is to push the nest around the stump and to guide it at the same time, and in that the force to be exerted manually by the operator is applied using only one hand and simply by closing the fingers onto a two-part handle, similar to the familiar bicycle brake, which enables a person able to use only one hand to position the device and to operate it without effort.

Thus in accordance with the invention this device for pulling on jersey sheaths for fitting contact prostheses which comprise a nest closed at one end at which an air extraction valve orifice is provided, said device including a bearing, is characterized in that said bearing is adapted to bear against said closed end of the prosthesis nest near said air extraction valve orifice on the nest so that the reaction to the pulling force is exerted at the point at which said bearing bears on said end.

In the following description the force amplifier means are similar to the familiar means used in guns for dispensing paste products (adhesive or mastic) which are sold in disposable tubular cartridges including a plastics material piston and a screw-on dispensing nozzle. Likewise, the means for holding the jersey sheath are similar in principle to the self-locking catches familiar on the gunwales of sailboats for locking sheets. These options, chosen for explanatory purposes and to clarify the appended drawings, are without prejudice to those employed in the actual implementation of the device in accordance with the invention.

BRIEF DESCRIPTION OF THE DRAWINGS

The following description given with reference to the appended drawings by way of non-limiting example only will enable a better understanding of the advantages, objects and features of the invention.

DETAILED DESCRIPTION OF THE INVENTION

Figure 1:
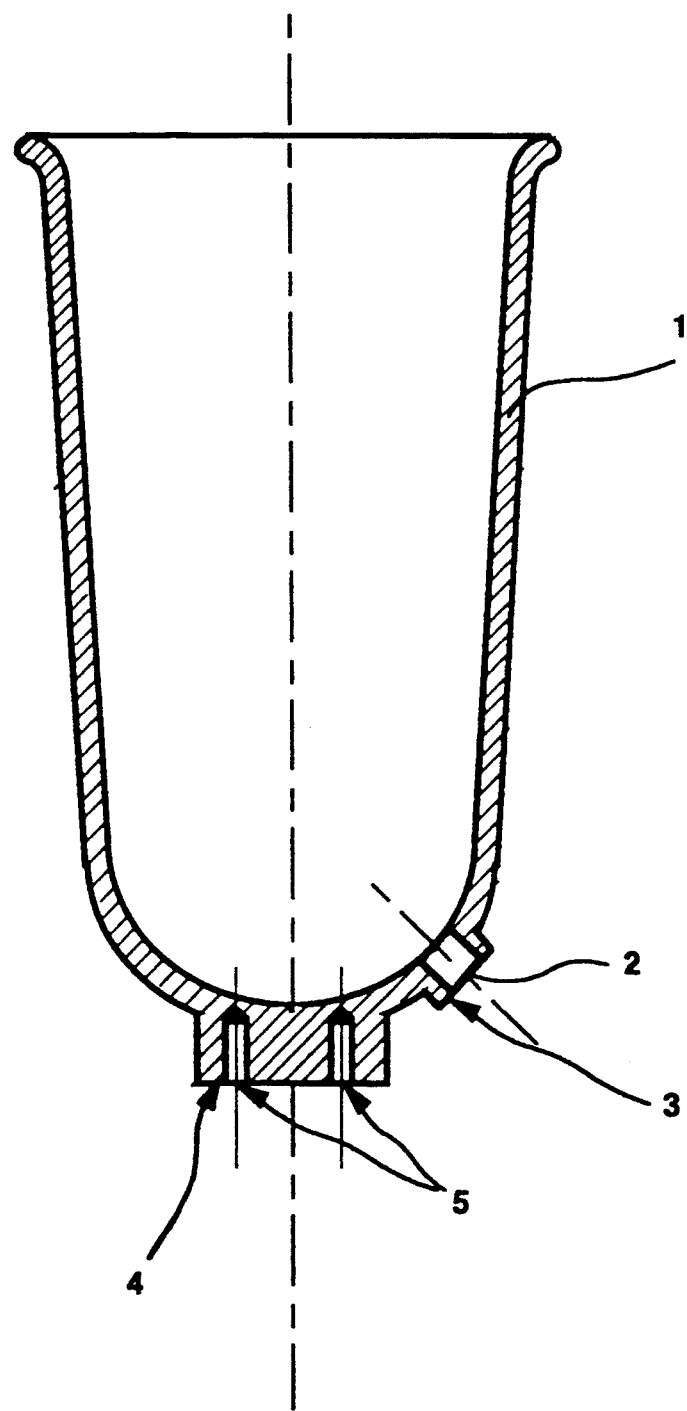
FIG. 1 shows in diagrammatic cross-section a contact prosthesis nest. This figure does not form part of the invention and it is included only to enable a better understanding of the elements with which the device in accordance with the present invention is in contact when it is operated.

FIG. 1 shows: a nest body 1 including an air extraction valve orifice 2 adapted to receive a removable valve (not shown) and which comprises a rubber plug adapted to nest in said orifice 2, the plug being fitted with a valve adapted to allow air to escape from the nest 1 during use of the prosthesis. The orifice 2 also has the jersey sheath passed through it to enable the sheath to be pulled out from the prosthesis nest 1. Outside the nest 1, the orifice 2 opens onto a strengthening boss having a circular annular flat 3.

At the lower end of the nest 1 is a fitting plane 4 perpendicular to the axis of the nest 1 designed to receive the artificial joint of the prosthesis which is fixed by screws inserted in threaded holes 5. The fitting plane 4 must be centered which explains why the opening of the valve 2 is off-center and oblique to the axis of the nest.

Figure 2:
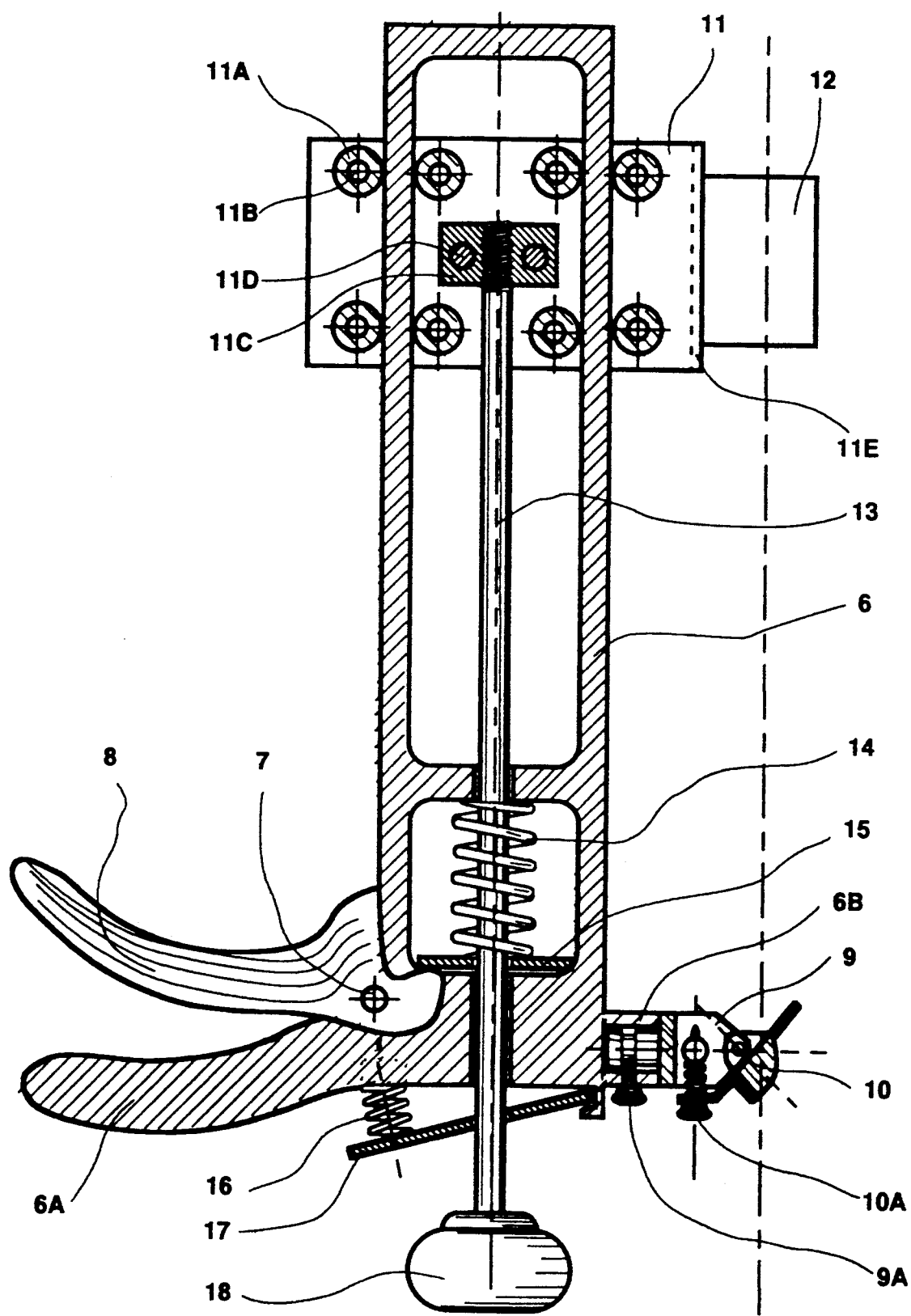
FIG. 2 is a general view of the device in partial cross-section providing an overview of its architecture and the relative position of its component parts.

FIG. 2 shows: a sliding frame 6, a fixed handle 6A, a bearing support collar 6B, a moving handle pivot pin 7, a moving handle 8, a bearing support 9, a screw 9A, an orientable bearing 10, a screw 10A, a pulling runner 11 formed of two flanges 11E, eight rollers 11A, eight pins 11B, a crossmember 11C and two rivets 11D, a self-locking catch 12, a push rod 13, a spring 14, a push tongue 15, a spring 16, a retainer tongue 17 and a retractor button 18.

Figure 3:
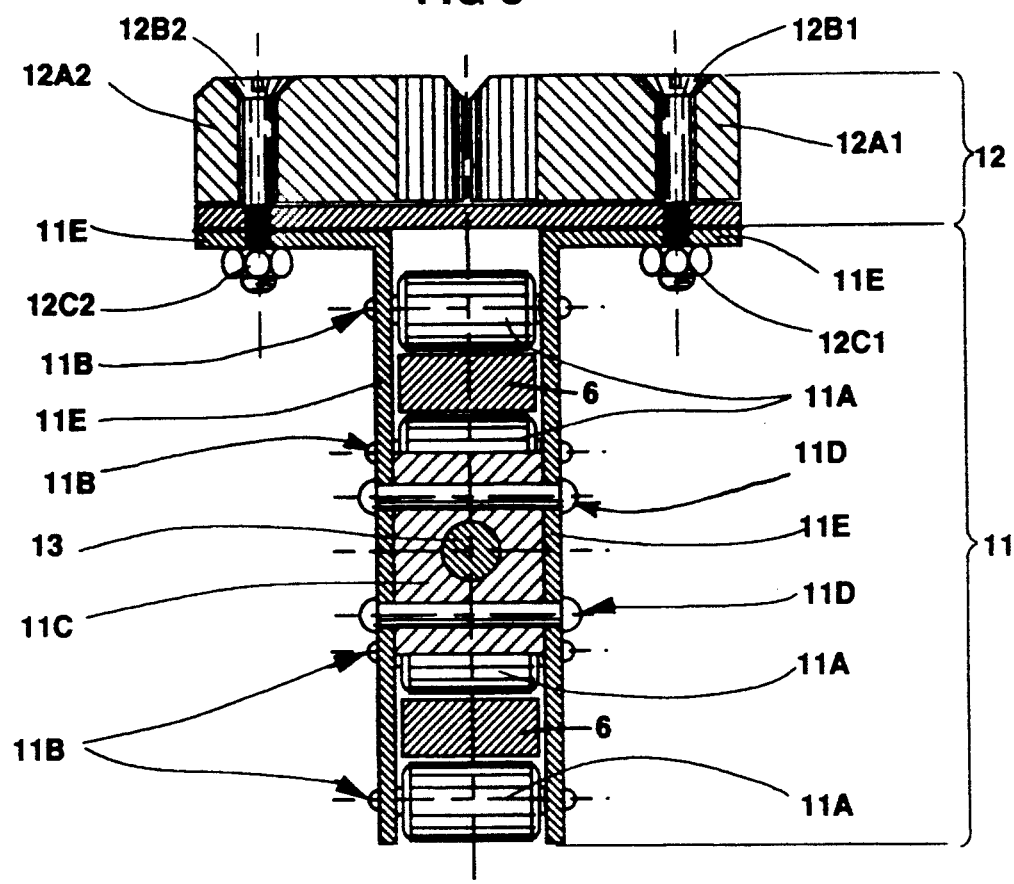
FIG. 3 shows the pulling runner of the device in cross-section in a plane perpendicular to the longitudinal axis of the device and the self-locking catch.

FIG. 3 shows: two L-shaped flanges 11E, four rollers 11A, four pins 11B, a crossmember 11C, two rivets 1D, a self-locking catch 12 comprising two notched cams 2A1 and 12A2, two pivot screws 12B1 and 12B2, two domed nuts 12C1 and 12C2, and a push rod 13. This figure also shows in cross-section the sliding frame 6.

Figure 4:
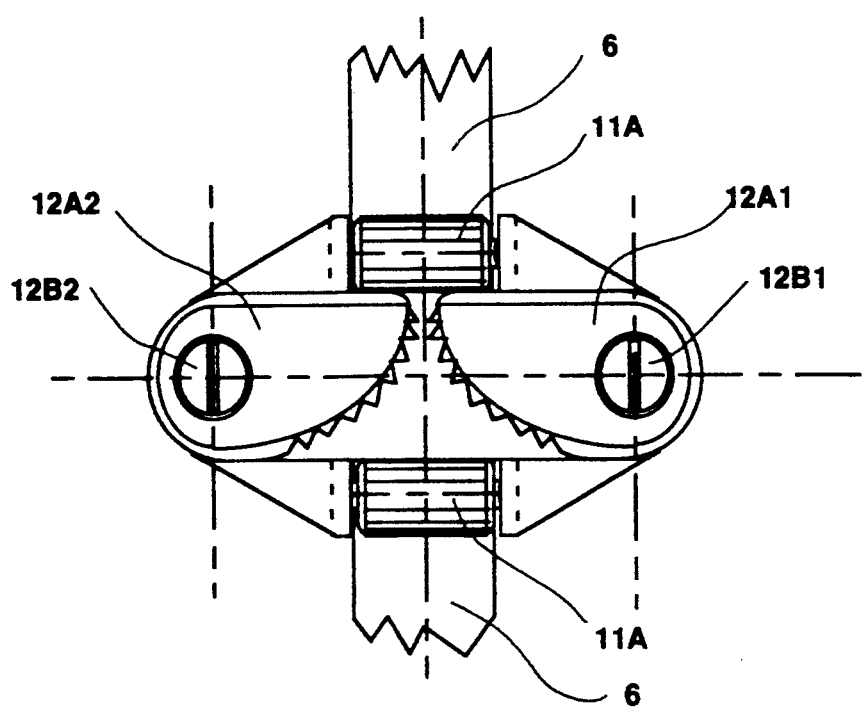
FIG. 4 is a top view of the runner and the self-locking catch.

FIG. 4 shows: the sliding frame 6 (in part), two of the rollers 11A, the two notched cams 12A1 and 12A2, the two screws 12B1 and 12B2.

Figure 5:
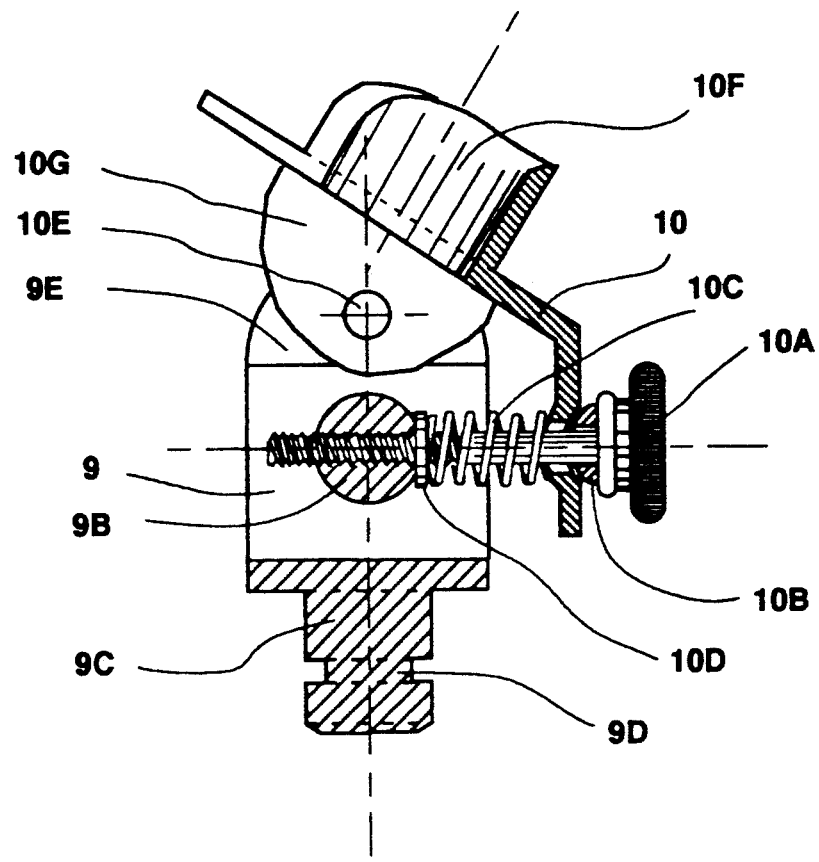
FIG. 5 shows the orientable bearing in elevation and partially in cross-section.

FIG. 5 shows: the bearing support 9, a transverse nut 9B, a cylindrical journal 9C with an annular groove 9D, two lugs 9E, the orientable bearing 10 comprising a centering flange 10F, the screw 10A, a dished washer 10B, a spring 10C, a flat washer 10D, two pins 10E, two flanges 10G.

Figure 6:
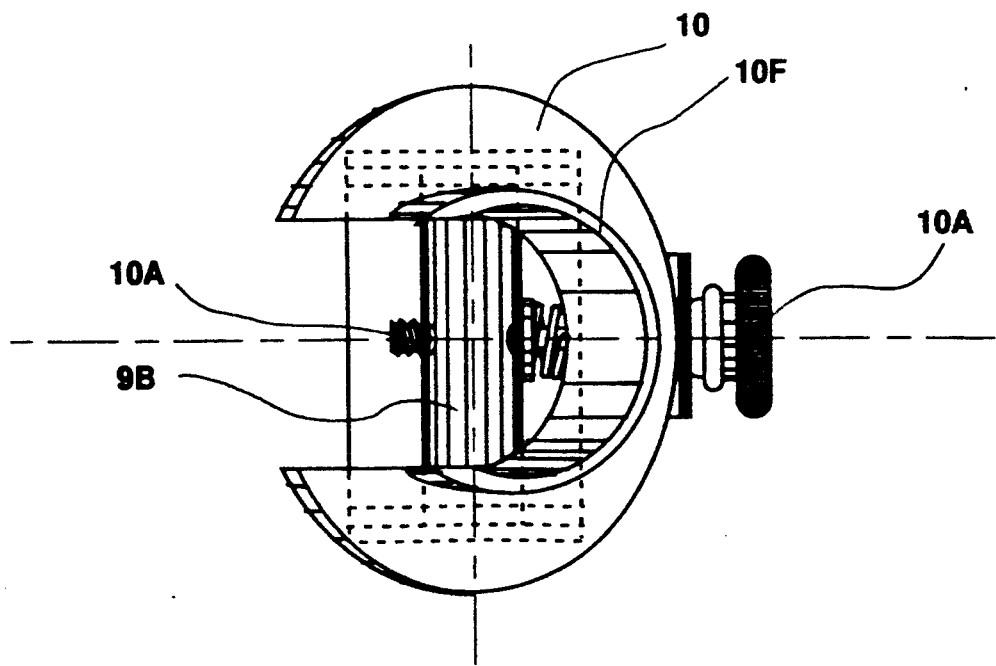
FIG. 6 is a top view of the orientable bearing.

FIG. 6 shows: the orientable bearing 10, the screw 10A, the flange 10F, the transverse nut 9B.

Figure 7:
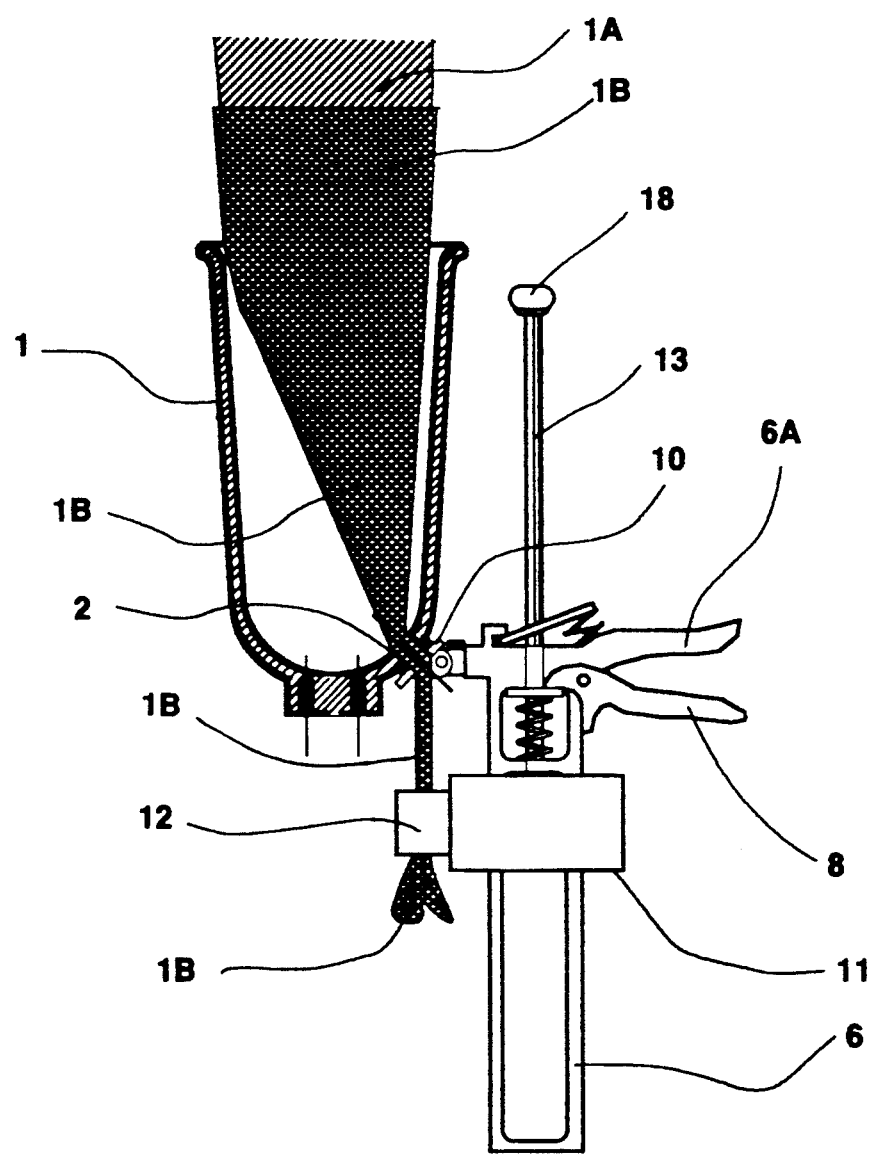
FIG. 7 is a partial diagrammatic cross-section of the device applied to a prosthesis nest at the start of operation of the device.

FIG. 7 shows: the prosthesis nest 1, the jersey sheath 1B, the stump 1A, the valve opening 2. These components although necessary for understanding the operation of the device do not form part of the invention. Opposite them is a simplified representation of the device showing the following parts: the sliding frame 6, the fixed handle 6A, the moving handle 8, the orientable bearing 10, the pulling runner 11, the self-locking catch 12, the push rod 13 and the retractor button 18.

Figure 8:
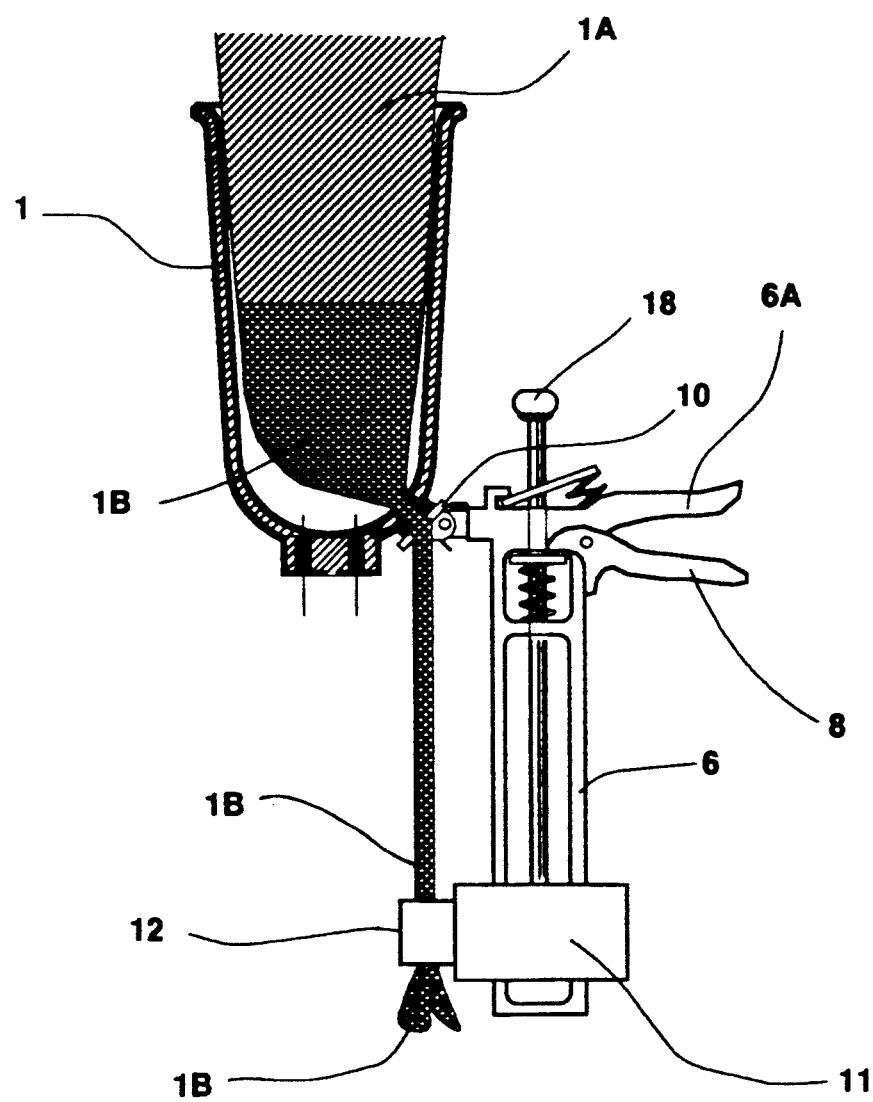
FIG. 8 shows the same items as the previous figure but at the end of operation of the device, just before the jersey sheath is pulled off the end of the stump and completely out through the nest.

FIG. 8 shows the same components as FIG. 7.

Figure 9:
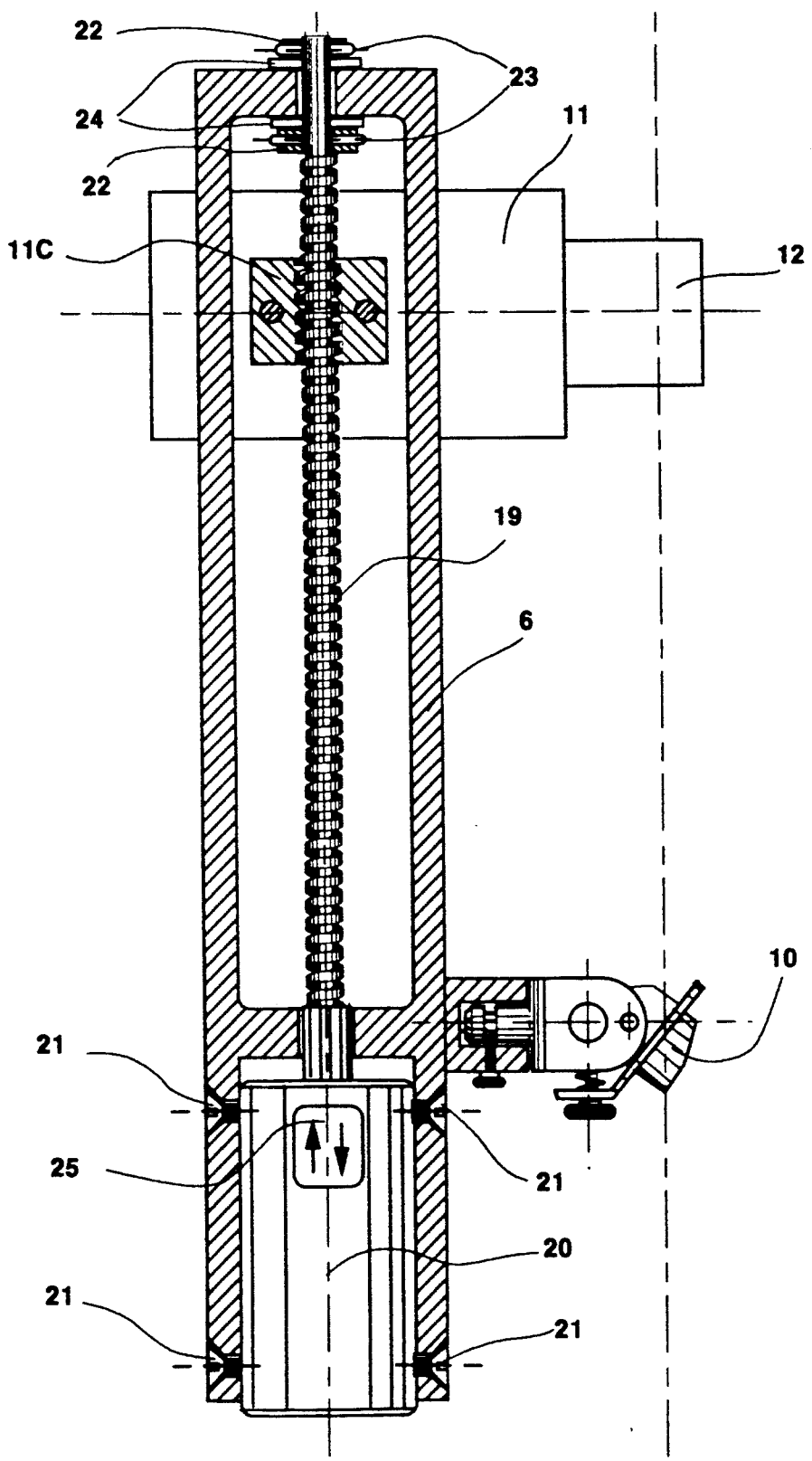
FIG. 9 shows an alternative embodiment of the device in which the traction force is provided by an electric motor similar to that of an electric screwdriver.

FIG. 9 shows: the sliding frame 6, the orientable bearing 10, the pulling runner 11, the crossmember 11C, the self-locking catch 12, an endless screw 19, an electric motor 20, four motor fixing screws 21, two endless screw annular thrust bearing plates 22, two conical pins 23, two flat antifriction washers 24 and a changeover switch 25.

The invention will now be described with reference to the appended drawings. FIG. 1, provided for information, does not require any more detailed description. Referring to FIG. 2, the sliding frame 6, the fixed handle 6A and the collar 6B may constitute a single part injection molded or cast in light alloy. The moving handle 8 can be made the same way. The push rod 13 will be of untreated mild steel or medium-carbon steel. The springs 14 and 16 are conventional coil springs which here operate in compression. The tongues 15 and 17 are made from steel and are quenched after machining to attain good resistance to wear by friction. These tongues are substantially rectangular, in the plane perpendicular to the cross-section plate of FIG. 2 and each pierced by a hole slightly larger than the diameter of the push rod 13 so that the latter can slide freely in them when the tongues are exactly in a plane perpendicular to its axis. Note that in FIG. 2 the retainer tongue 17 is oblique to the axis of the rod 13 which prevents the latter from being retracted. On the other hand, it could move forward because the entrainment by friction of the tongue 17 would pivot the latter, compressing the spring 16. Pivoting of the handle 8 about its pin 7 draws forward the thrust tongue 15 which, held back by the spring 14, assumes an oblique position and so draws the push rod 13 forward. This mechanism is well known and will not be described in more detail. Each time the handle 8 is pulled back the rod 13 is advanced by one step. At the end of its forward travel the operator grasps the button 18 and pulls it back, holding only the fixed handle 6A in the other hand and simultaneously pushing with the thumb on the longer part of the tongue 17. This enables the push rod 13 to be pulled completely back. The push rod 13 is screwed into the crossmember 11C of the puller 11 which is fastened to the puller by the rivets 11D which pass through the flanges 11E. The pulling runner 11 is thus attached to the push rod 13 and moved with it.

The design of the pulling runner 11 is explained with reference to FIGS. 2, 3 and 4. It comprises the two L-shaped flanges 11E joined together by the rivets 11D of the crossmember 11C. The latter is slightly thicker than the width of the sliding frame 6 so that sufficient clearance remains between the inside surface of the L-shaped flanges 11E and the flanks of the slideways of the frame 6 for the carriage 11 to be guided but still able to move. The eight rollers 11 may be machined from a high-strength professional grade plastics material having good anti-friction properties. Their thickness will be slightly less than that of the crossmember 11C so that they can rotate freely between the L-shape flanges 11E on the pins 11B. The bore of the rollers 11A will be slightly greater than the diameter of the pins 11B so that the former can rotate freely on the latter. The total length of the pins 11B will be equal to the thickness of the crossmember 11C plus twice the thickness of a flange 11E plus twice the length required to enable them to be preened over from the outside of the flanges 11E. The part of the pins 11B passing through the flanges 11E will have a diameter less than that of the central part so that when the pins 11B are peened over on the outside of the flanges 11E the center part of the pins 11B will also serve as a spacer between the two flanges 11E.

The self-locking catch 12 is fixed by the screws 12B1 and 12B2 to the bent over part of the L-shape of the flanges 11E. The self-locking catch is spring-loaded by springs which urge the notched cams 12A1 and 12A2 onto internal abutments (not shown) and will not be described in more detail because it is of a well known type.

The design of the orientable bearing 10 is explained with reference to FIGS. 5 and 6. The bearing 10 may be die stamped from a ductile material which retains high strength after hardening. Its outside diameter is substantially equal to that of the flat 3 in FIG. 1 and it is adapted to bear against the latter. The flange 10F has an outside diameter slightly less than the diameter of the valve opening 2 (FIG. 1) and is adapted to enter the opening 2 to center the bearing 10 on the flat 3. The bearing 10 comprises two flanges 10G one on either side of the bearing and opposite the flange 10F to form a yoke which is articulated by the two pins 10E to the lugs 9E of the bearing support 9. The disposition of the knurled head screw 10A, the transverse nut 9B, the dished washer 10B, the spring 10C (which operates in compression) and the flat washer 10D enables the inclination of the orientable bearing 10 to be varied by screwing in or unscrewing the screw 10A. The journal 9C of the bearing support 9 locates it in the hole in the bearing support collar 6B (see FIG. 2) to enable orientation in azimuth of the bearing 10 by operating manually on the bearing support 9. Once the required orientation is obtained the screw 9A is locked again which maintains the required adjustment. This facility to orient the bearing 10 in elevation and in azimuth enables the device in accordance with the invention to be used on prosthesis nests having different orientations of the valve opening 2. Note that the bearing 10 and the flange 10F are open and similar to a two-pronged fork, which makes it possible to fit the bearing 10 over the jersey sheath without it being necessary to thread the latter into the bearing 10.

The use of the device is described with reference to FIGS. 7 and 8. FIG. 7 shows the device at the start of the fitting operation and in it a jersey sheath 1B has been threaded over the stump 1A and then inserted via the interior of the prosthesis nest through the valve opening 2. The device has been fitted against the prosthesis nest 1 and bears against the flat at the opening 2 through the intermediary of the orientable bearing 10. The free end of the jersey sheath 1B outside the nest 1 passes through the bearing 10 and has been locked into the self-locking catch 12 fastened to the pulling runner 11 which is in its rearmost position, the thrust rod 13 having been pulled fully back beforehand by means of the button 18. In this condition the device is ready for use. The operator presses the moving handle 8 against the fixed handle 6A the effect of which is to move the push rod 13 forward by one step which advances commensurately the pulling runner 11 and the self-locking catch 12. The latter pulls on the jersey sheath 1B and the reaction to this traction force pushes the nest 1 towards the stump 1A. The operator presses in the mobile handle 8 as many times as necessary until the device is in the configuration shown in FIG. 8. If the pulling runner 11 reaches the end of its maximum travel before the jersey sheath 1B is completely removed from the nest 1 all that the operator has to do is to detach the jersey sheath 1B from the self-locking catch 12, return the device to the starting position as shown in FIG. 7 and then lock the jersey sheath 1B into the self-locking catch 12 again and resume pulling on the sheath.

FIG. 9 shows an alternative embodiment of the device which operates in the following manner: a motor 20 similar to those of electric screwdrivers, preferably powered from a battery, drives the endless screw 19 so that it rotates in one direction or the other according to how the operator sets the changeover switch 25. The effect of this is to move the pulling runner in one direction or the other and to arrive at the same result as when using the manual version of the device. Note that the circular abutment bearing rings 22 at each end of the sliding frame 6 provide bearing points for the endless screw which has the advantage of causing the latter to operate in traction when the pulling runner 11 is moved in the direction in which it actually pulls on the jersey sheath 1B. This simultaneously compresses the sliding frame 6 whose injection molded metal is better suited to withstanding this type of load.

Figure 10:
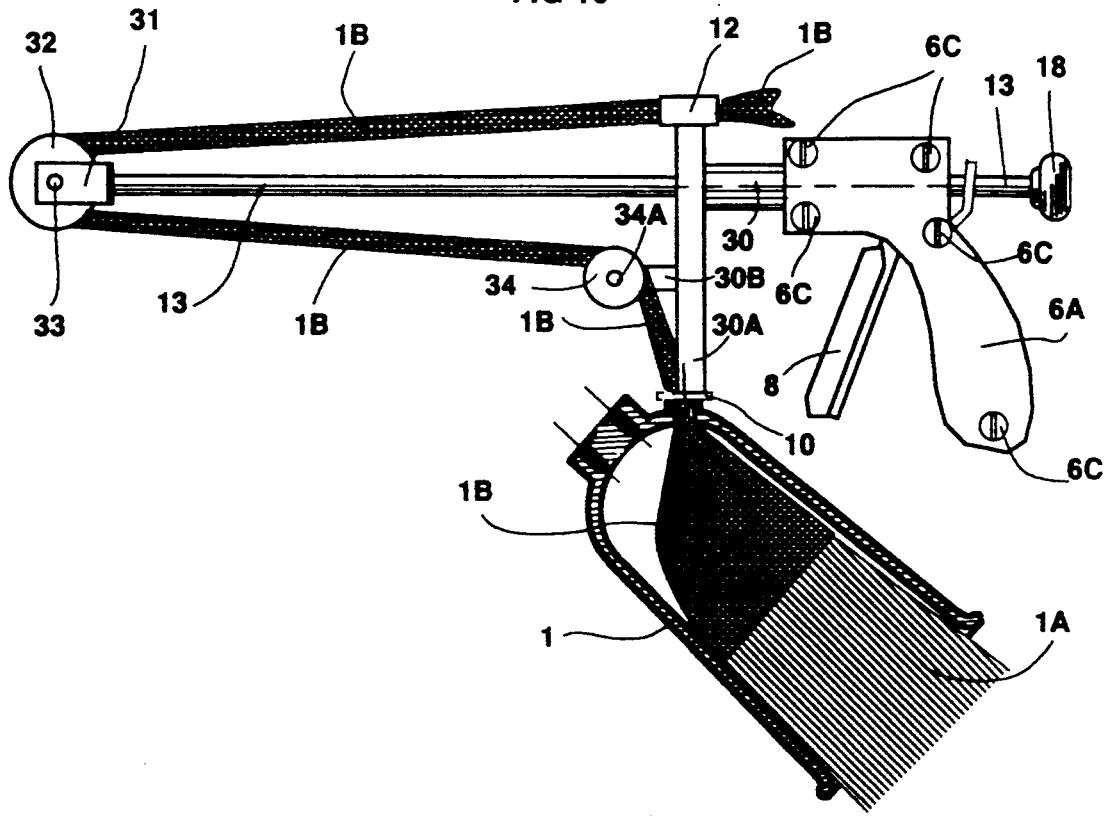
FIG. 10 shows a first embodiment of the device at the end of the operation to extract the jersey sheath 1B.

FIG. 10 shows: the prosthesis nest 1 and the stump 1A (shown in part), the jersey sheath 1B, the air extraction valve opening 2, the fitting plane 4, the sliding frame 6, the fixed handle 6A, five screws 6C, the moving handle 8, the bearing 10, the self-locking catch 12, the push rod 13, the retainer tongue 17, the retractor button 18, a spacer 30, a spacer 30A, an off-center finger 30B, a yoke 31, a pulley wheel 32, a pin 33, a pulley wheel 34 and a pulley wheel pin 34A.

In this first embodiment the sliding frame 6 is shortened and in this case is manufactured in two symmetrical half-shells assembled together by the screws 6C. The push rod is much longer than the sliding frame 6. At the end opposite the retractor button 18 the rod 13 is fastened to a yoke 31 which carries a grooved pulley wheel 32 made from a lightweight material and which rotates on the pin 33 carried by the yoke 31. The pulley wheel 32 has a semicircular peripheral groove to receive and guide the jersey sheath 1B. The orientable spacer 30 is tubular, of cylindrical cross-section and is turned from a lightweight material. It is retained in the sliding frame by two half-bearings (one per half-shell) concentric with the axis of the push rod 13. The spacer 30 can rotate in the two half-bearings if the screws 6C are loosened and is locked in position when the same screws 6C are tightened. The spacer 30 incorporates a circular cross-section axial bore for the push rod 13 to pass through. The spacer 30 is fastened to the spacer 30A which carries the self-locking catch 12 at its upper end and the bearing 10 at its lower end. The spacer 30A carries the off-center finger 30B which supports, cantilever fashion, the pin 34A on which the pulley wheel 34 rotates. There is a hole in the spacer 30A the same diameter as the spacer 30 and facing the latter. The pulley wheel 34 is of identical design to the pulley wheel 32. In this embodiment the push mechanism is contained within the two half-shells which form the sliding frame 6 and is therefore not visible. It is similar in design to that described with reference to FIG. 2 and the push rod 13 is moved forward by one step each time that the moving handle 8 is pulled back relative to the fixed handle 6A.

The operation of this first embodiment of the device is as follows: firstly, the push rod 13 is pulled out to its rearmost position using the retractor button 18. This causes the yoke 31 to abut against the spacer 30A. After threading the jersey sheath 1B over the stump 1A and threading the end part of the jersey sheath 1B through the opening 2 via the interior of the prosthesis nest 1 the operator positions the bearing 10 on the opening 2 and places the jersey sheath 1B successively into the groove of the pulley wheel 34 and then into the groove of the pulley wheel 32 before fixing it into the self-locking catch 12. The operator then presses the moving handle 8 against the fixed handle 6A which moves the yoke 31 away from the spacer 30A and so pulls on the jersey sheath 1B which draws the stump 1A into the nest 1. This operation is repeated as many times as necessary to extract the jersey sheath 1B completely from the nest 1.

FIG. 11 shows:

the prosthesis nest 1 and the stump 1A (shown in part), the jersey sheath 1B, the air extraction valve opening 2, the fitting plane 4, the fixed handle 6A, the moving handle 8, the bearing 10, a casing 40, two rollers 1, 42, the tube 43, a spacer 44 and a cable sheath 45.

The assembly formed by the fixed handle 6A, the moving handle 8, the tube 43 and the cable sheath 45 is very similar to half the handlebars of a bicycle and can be made the same way, namely: the tube 43 carries the handle 6A and the handle 8, one end of the cable sheath 45 is abutted against the fixed part of the moving handle 8 and its other end is abutted on the casing 40, it contains a cable (not shown) which operates the mechanism driving the rollers 41 and 42. The handle may be oriented about the tube 43 and fixed in position, once adjusted, in the same way as a brake control lever on a bicycle. The tube 43 is fastened to the casing 40. This may be injection molded or cast in light alloy. It carries the mechanism driving the two rollers 41 and 42. This drive mechanism has two functions:

1—It rotates the rollers 41 and 42 through the same angle each time the handle 8 is pressed, but in opposite directions; in other words the roller 41 turns through a given angle anticlockwise and simultaneously the roller 42 turns through the same angle clockwise; the two rollers are provided with "freewheel" type mechanisms which allow them to rotate only as previously described and prevent them rotating in the opposite direction.

2—It presses the rollers 41 and 42 together; a handle (not shown) is used to move the two rollers 41 and 42 apart; the spacer 44 is fastened to the casing 40, is made from a tube or a profile that is not fully closed and carries at its lower end the bearing 10 to which it is fastened.

This second embodiment of the device operates as follows: after threading the jersey sheath 1B over the stump 1A and after threading the free end of the jersey sheath 1B into the opening 2, as previously, through the interior of the prosthesis nest 1, the operator positions the bearing 10 on the opening 2 and passes the jersey sheath 1B between the rollers 41 and 42, having first moved them apart by operating the handle that is not shown, after which he releases the handle so that the rollers 41 and 42 grip the jersey sheath. The operator then presses the handle 8 against the handle 6A as many times as necessary for the entrainment of the jersey sheath by the opposite-direction rotation of the two rollers 41 and 42 to extract it completely from the prosthesis nest 1.

ADVANTAGE RESULTING FROM USE OF THE PRESENT INVENTION

The advantages of the present invention will be summarized below.

In the basic, manually operated version the force to be exerted by the hand of the operator is reduced by a factor of 4 to 6 as compared with that required to pull directly on the jersey sheath 1B by hand. This hand pressure, exerted simply by closing the fingers around the two-part handle 8/6A, serves only to generate the traction force, the force required to hold the jersey sheath being eliminated by virtue of the self-locking catch 12.

From the ergonomical point of view, the position of the operating handle 8/6A is ideal either for the amputee himself or for a third person.

The device simultaneously pulls on the jersey sheath 1B and guides the prosthesis nest 1 towards the stump 1A, pushing the former towards the latter.

In the basic, manually operated version the device provides "feel" (tactile feedback) in that the operator can tell from the force required on the handles 6A how strongly the jersey sheath 1B is gripped between the inside of the nest 1 and the stump 1A and, if this is excessive, remedy it by putting only part of the jersey sheath 1B into the self-locking catch 12 or by shifting the stump 1A in small circular movements to free off the sheath 1B. The sheath remains tensioned due to its own elasticity if the traction force is interrupted and because of this the sheath is released and moves on its own as soon as the small circular movements mentioned above free it, without it being necessary to operate simultaneously the handles 8/6A. The operator therefore has only one thing to do at a time.

The holding of the jersey sheath 1B in the self-locking catch 12 is extremely simple and is effected from the side (in passing) in the same way as for locking the sheets on sailboats. It is possible to wedge in only part of the perimeter of the jersey sheath 1B, as is routine practice.

Given the ease and speed with which the jersey sheath is held in the self-locking catch, it is possible to produce devices having a short sliding frame 6, and therefore a reduced travel, and to carry out the operation in a number of consecutive pulls. In this case it would be possible to produce compact and lightweight devices for amputees who fit their prosthesis only once each day and to provide longer devices, enabling the sheath to be pulled out in one operation, for intensive use in specialist establishments.

Great ease of fitting the device to the valve opening of the prosthesis nest 1 after the jersey sheath 1B has been passed through the opening 2 and without requiring the jersey sheath 1B to be threaded into the bearing 10 because the latter is open and is rather like a two-pronged fork which is merely placed over the jersey sheath 1B where it exits the valve opening 2 of the prosthesis nest 1, before inserting the flange 10F in the opening 2.

Bearing 10 orientable in elevation and in azimuth, enabling the device to be used on prostheses whose valve openings are differently oriented.

In the battery-powered electric motor version, using a similar motor to electric screwdrivers, the manual force is eliminated but the tactile feedback effect is reduced. However, this type of motor has limited torque. After a little practice the operator can tell how stuck the jersey sheath 1B is according to the speed of the motor 20 and changes in the noise it makes as it operates. This design may be reserved to amputees having difficulty in applying even very small manual forces.

The advantages of the embodiment shown in FIG. 10 are as follows:

Each time the handle 8 is pressed the jersey sheath 1B is pulled by twice the amount that the push rod 13 is advanced, which means that the latter may be half as long to pull out the same amount of jersey sheath 1B.

The sliding frame 6 can pivot 360° around the spacer 30, whereby the device is adaptable to all anatomical differences both of the handicapped person himself and a third person assisting him.

The pulley wheel 34 changes the direction of the reaction to the traction force at the bearing 10 and the opening 2 around which it is seated. There is virtually no horizontal component of force at the opening 2 and the bearing 10 is pushed substantially along the axis of the opening 2.

Figure 11:
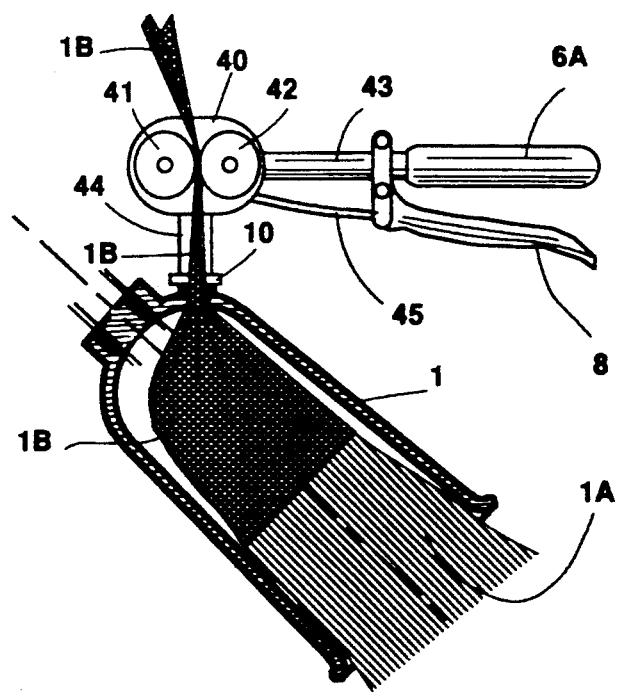
FIG. 11 shows a second embodiment of the device at the end of the operation to extract the jersey sheath 1B.

The advantages of the second embodiment shown in FIG. 11 are as follows:

The complete device may be very short because the push rod 13 is eliminated.

At the end of operation the device does not need to be returned to the starting position It utilizes known means proven on millions of bicycles.

I claim:

1. Apparatus for fitting a stump of a body member to a rest of a prosthesis having an open end for inserting the stump and a closed end against which the stump is adapted to bear, in which a jersey sheath is wrapped at least partly round the stump and threaded through an air exhaust opening at the closed end of the nest, said apparatus having a common support and comprising, mounted on the common support, traction means for applying traction force to the sheath for drawing the stump to the closed end of the nest, a bearing member bearing engageable with the nest in the immediate vicinity of the air exhaust opening for exerting a reaction force on the nest in response to the traction force applied by the traction means, and control means for controlling traction force applied by the traction means.

2. Apparatus according to claim 1, wherein said traction means comprising a traction member having means for fastening said jersey sheath and drive means for driving said traction member.

3. Apparatus according to claim 1, wherein said bearing member includes a passageway for the jersey sheath immediately adjacent said air exhaust opening.

4. Apparatus according to claim 3, wherein said passageway is part annular.

5. Apparatus according to claim 1, further comprising means for adjusting said bearing member relative to the common support in elevation and in a azimuth.

6. Apparatus according to claim 1, wherein the bearing member penetrates into the air exhaust opening.

7. Apparatus according to claim 1, wherein the bearing member has flange means for centering it relative to the air exhaust opening in the next.

8. Apparatus according to claim 1, wherein the bearing member is in bearing engagement around the air exhaust opening.

9. Apparatus according to claim 2, wherein said apparatus comprises a portable unit, and said drive means for said traction member comprising an electric motor.

10. Apparatus according to claim 9, further comprising are chargeable battery means for powering the electric motor, and a charger including a rack for mounting the portable unit.

11. Apparatus according to claim 2, wherein the traction member is mounted for movement on the common support in opposed directions for selectively increasing and relaxing the traction force applied to the jersey sheath, said drive means including a reversible motor, and said control means controlling the direction of rotation of the motor.

12. Apparatus according to claim 2, wherein said common support comprises an elongate frame, the traction member being mounted for rectilinear reciprocating movement on said elongate frame, and said drive means comprising an endless screw threadedly engaging the traction member for movement along the elongate frame.

13. Apparatus according to claim 2, wherein said means for fastening comprises a self-locking catch for retain the jersey sheath firmly over at least part of its cross-section.

14. Apparatus according to claim 2, wherein said apparatus is a portable unit having a handle mounted on the common support, said control means being mounted on said handle, said traction member being mounted for rotation on the common support and driven for rotational movement by said drive means, said common support including an arm extending away from the handle, said bearing member being disposed at the end of said arm.

15. Apparatus according to claim 1, wherein said traction means comprises a pusher system and a two-part handle including a fixed branch fixed relative to the bearing member and a branch movable with respect to the fixed branch.

16. Apparatus according to claim 2, wherein said means for fastening is mounted on the common support which comprises a frame, said drive mans comprising a push rod reciprocally mounted on the frame, said traction means including a grooved pulley carried by the push rod and engaging the jersey sheath for applying the traction force thereto.

17. Apparatus according to claim 1, wherein the traction means comprises a pair of rollers rotatable in opposite directions for gripping the jersey sheath therebetween, and a mechanism for rotating the rollers in response to repeated actuation of a moving handle relative to a fixed handle on the common support.

* * * * *